United States Patent
Pearson et al.

(10) Patent No.: US 6,531,608 B2
(45) Date of Patent: Mar. 11, 2003

(54) VARIOUS THIOL COMPLEXES, PROCESSES FOR THEIR SYNTHESIS AND CLINICAL APPLICATIONS

(75) Inventors: Don C. Pearson, Lakewood, WA (US); Kenneth T. Richardson, Anchorage, AK (US)

(73) Assignee: Chronorx, LLC., Anchorage, AK (US)

( * ) Notice: Subject to any disclaimer, the term of this patent is extended or adjusted under 35 U.S.C. 154(b) by 0 days.

(21) Appl. No.: 10/167,630

(22) Filed: Jun. 11, 2002

(65) Prior Publication Data

US 2002/0151533 A1 Oct. 17, 2002

Related U.S. Application Data

(62) Division of application No. 09/564,070, filed on May 3, 2000, now Pat. No. 6,429,219.
(60) Provisional application No. 60/136,197, filed on May 25, 1999.

(51) Int. Cl.$^7$ ............... C07D 277/02; C07C 321/04; C07F 1/08; C07F 3/02; C07F 3/06
(52) U.S. Cl. ............... 548/182; 556/45; 556/110; 556/118; 562/557
(58) Field of Search ............... 548/182; 556/45, 556/110, 118; 562/557

(56) References Cited

PUBLICATIONS

Jay, M.T. et al. "Physiological Society Symposium: Impaired Endothelial and Smooth Muscle Cell Function in Oxidative Stress. Modulation of Vascular Tone by Low Density Lipoproteins: Effects on L–Arginine Transport and Nitric Oxide Synthesis," *Exper. Physiol.* 1997, pp. 349–360, vol. 82.

Kotler, M. et al., "Melatonin Increases Gene Expression for Antioxidant Enzymes in Rat Brain Cortex," *J. Pineal. Res.* 1998, pp. 83–89, vol. 24.

Lüscher, T.F. and Tanner, F.C. "Endothelial Regulation of Vascular Tone and Growth," *AJH* 1993, pp. 283S–293S, vol. 6.

Meyer, P. et al. "Effects of Calcium Channel Blockers on the Reponse to Endothelin–1, Bradykinin and Sodium Nitroprusside in Porcine Ciliary Arteries," *Exp. Eye Res.* 1995, pp. 505–510, vol. 60.

Nathanson, J.A. and McKee, M. "Alterations of Ocular Nitric Oxide Synthase in Human Glaucoma," *Invest. Ophthalmol. Vis. Sci.* 1995, pp. 1774–1784, vol. 36, No. 9.

Noske, W. et al. "Endothelin–Like Immunoreactivity in Aqueous Humor of Patients with Primary Open–Angle Glaucoma and Cataract," *Graefe's Arch. Clin. Exp. Ophthalmol.* 1997, pp. 551–552, vol. 235.

Reaven, G.M. "Pathophysiology of Insulin Resistance in Human Disease," *Physiological Rev.* Jul. 1995, pp. 473–486, vol. 75, No. 3.

Tanner, F.C. et al. "Endothelium–Derived Nitric Oxide, Endothelin, and Platelet Vessel Wall Interaction: Alterations in Hypercholesterolemia and Atherosclerosis," *Seminars in Thrombosis & Hematosis* 1993, pp. 167–175, vol. 19, No. 2.

Tezel, G. et al. "Plasma and Aqueous Humor Endothelin Levels in Primary Open–Angle Glaucoma," *J. Glaucoma* 1997, pp. 83–89, vol. 6.

Vita, J.A. et al. "L–2–Oxothiazolidine–4–Carboxylic Acid Reverses Endothelial Dysfunction in Patients with Coronary Artery Disease," *J. Clin. Invest.* Mar. 1998, pp. 1408–1414, vol. 101, No. 6.

Abdo et al. "Antioxidative Effect of Na–Mercaptopropionylglycine (Nc MPG) in Experimental Acute Pancreatitis," *Rev. Hosp. Clin. Fac. Med. Sao Paulo* 1998; pp. 169–173, vol. 53, No. 4.

Adnot, S. et al. "Nitric Oxide, from Vascular Physiology to Therapeutics," *Arch, Mal. Coeur.* 1994; pp. 41–51, vol. 87, No. 4.

Bains, S. and Shaw, C.A. "Neurodegenerative Disorders in Humans: The Role of Glutathione in Oxidative Stress–Mediated Neuronal Death," *Brain Res. Rev.* 1997, pp. 335–358, vol. 25.

Chen, H. and Tappel, A.L. "Vitamin E, Selenium, Trolox C, Ascorbic Acid Palmitate, Acetylcysteine, Coenzyme Q, β–Carotene, Canthaxanthin, and (+)–Catechin Protect Against Oxidative Damage to Kidney, Heart, Lung and Spleen," *Free Rad. Res.* 1995, pp. 177–186, vol. 22, No. 2.

Cioffi, G.A. et al. "An In Vivo Model of Chronic Optic Nerve Ischemia: The Dose–Dependent Effects of Endothelin–1 on the Optic Nerve Microvasculature," *Curr. Eye Res.* 1995, pp. 1147–1153, vol. 14, No. 12.

Haefliger, I.O. et al. "Nitric Oxide and Endothelin–1 are Important Regulators of Human Opthalmic Artery," *Invest. Ophthalmol. & Visual Sci.* Jun. 1992, pp. 2340–2343, vol. 33, No. 7.

Harrison, D.G. "Endothelial Dysfunction in Atherosclerosis," *Basic Res. Cardiol.* 1994, pp. 87–102, vol. 89, Suppl. 1.

*Primary Examiner*—Taofiq Solola
(74) *Attorney, Agent, or Firm*—Townsend and Townsend and Crew, LLP

(57) ABSTRACT

This invention relates to the synthesis of certain complexes of cysteine, N-acetylcysteine, N-(2-mercaptopropionyl) glycine, and L-2-oxothiazolidine-4-carboxylate and to the nutritional use of these and other related individual or complexed thiol-contributing glutathione predecessors. Clinical uses for these molecules and complexes in the beneficial modification of various physiological conditions and functions associated with aging, chronic glaucoma, diabetes mellitus, insulin resistance, macular degeneration, neurodegenerative diseases and vasoconstriction are described in particular.

20 Claims, No Drawings

VARIOUS THIOL COMPLEXES, PROCESSES FOR THEIR SYNTHESIS AND CLINICAL APPLICATIONS

CROSS REFERENCE TO RELATED APPLICATION

This application is a Division of 09/564,070 filed May 3, 2000 now U.S. Pat. No. 6,429,219 and related to U.S. Provisional Patent Application No. 60/136,197, filed May 25, 1999, and claims all benefits legally available therefrom. Provisional Patent Application No. 60/136,197 is hereby incorporated by reference for all purposes capable of being served thereby.

BACKGROUND OF THE INVENTION

This invention is in the fields of pharmacology and biochemistry. It relates to the synthesis of certain complexes of L-cysteine, N-acetyl L-cysteine, N-(2-mercapto-propionyl)glycine, L-2-oxothiazolidine-4-carboxylate and the nutritional or clinical use of these and other related individual or complexed thiol contributing, glutathione predecessors. The use of these molecules and complexes in clinical presentations of chronic glaucoma, diabetes mellitus, macular degeneration, neurodegenerative diseases and vasoconstriction are described in particular.

I. Clinical Review
A. Chronic Glaucoma

The eye is maintained in a homeostatic shape by a relatively stable intraocular pressure (IOP) that varies within a reasonably narrow range so long as the intraocular production of aqueous fluid remains equal to its exit from the eye.

The optic nerve head can tolerate relatively high levels of IOP if the availability of oxygen from posterior ciliary arteries and optic nerve head arterioles remains adequate. However, if the global intraocular pressure is higher than the perfusion pressure driving oxygen through the arteriole into the surrounding tissues, decreasing amounts of oxygen will reach the optic nerve head and nerve disability will result.

Similarly if nerve head arterioles are unable to provide sufficient volumes of blood to the optic nerve, dysfunction will follow. These arteriolar deficiencies may occur because of: vasoconstriction secondary to generalized or localized microvascular dysregulation, arteriolar muscular hypertrophy (perhaps as a result of chronic spasm), atherosclerotic luminal reduction, changes in the viscosity or laminar flow patterns of the arterial blood or in either essential or iatrogenic systemic hypotension.

Glaucoma in various guises affects a large segment of the public. It is estimated that 2% to 2.5% of the population over the age of 40 has chronic open angle glaucoma (COAG). This is the most common form of glaucoma.

Because optic nerve damage occurs in patients with chronically elevated IOP, present treatments concentrate on reducing this objective finding by a variety of modalities: topical eye drops, oral medications, intravenous medications, surgical procedures, laser phototherapy, etc. All of these focus upon the reduction of pressure inside the eye and rely upon this pressure reduction to prevent optic nerve damage. For many patients this approach is effective. However, the effectiveness of each of these treatments runs from total ineffectiveness, progressive optic atrophy and eventual blindness, to an arrest of the disease, complete cessation or prevention of further optic nerve failure and preservation of vision.

Factors other than IOP levels influence the clinical outcome for many glaucoma patients. This invention is focused upon two alternatives: a) hypovascularity of the optic nerve head and loss of the vascular integrity of the optic nerve resulting in glial collapse, ganglion cell apoptosis and progressive neural atrophy with visual loss; b) hypoxia-induced free radical interference with retrograde axoplasmic flow within the optical neural axons.

Ocular Microvascular Regulation

A balanced biochemistry of nitric oxide (NO) and endothelin-1 (ET-1) mediates local optical blood flow and many facets of systemic vascular autoregulation.

NO is a highly soluble gas formed within endothelial cells by the action of the constitutive enzyme nitric oxide synthetase (cNOS). NO activates guanylate cyclase and increases guanosine-monophosphate (cGMP) within the vascular musculature. cGMP produces relaxation and dilatation of vessels. It also has more generalized smooth muscle relaxing abilities; in this regard it relaxes the contractile trabecular elements of the eye, increases aqueous outflow and reduces IOP. Levels of NO in the trabecular region of eyes of glaucoma patients are lower than in the eyes of non-glaucoma patients. Aging and atherosclerotic dysfunction of the vascular endothelium reduce its ability to produce NO because of reduced local levels of cNOS.

ET-1 is also formed within and secreted by endothelial cells. ET-1 reacts with local receptors on smooth muscle cells to produce a powerful and long-lasting vasoconstriction. ET-1 is particularly released by aged or unhealthy endothelial cells, e.g., in the presence of atherosclerosis or in the presence of local collections of endothelial leukocytes or platelets, etc. The smooth muscle contraction produced by ET-1 strongly opposes the relaxation properties of NO and trabecular contraction is stimulated, resistance to aqueous outflow is increased and IOP increases. Aqueous levels of ET-1 are elevated in glaucomatous eyes. Induced elevations of aqueous ET-1 levels produce optic nerve collapse.

This balance between NO and ET-1 mediates the autoregulation of blood flow within the optic nerve and throughout the peripheral circulation.

Exposure of patients to calcium channel blockers has resulted in an improvement of some glaucomatous visual fields. Vascular endothelial production of ET-1 is dependent upon cytosolic calcium ($Ca^{2+}$) influx via transmembrane calcium channels. Calcium channel blockade reduces this $Ca^{2+}$ influx and reduces the production of ET-1. A serendipitous reduction of IOP has been observed as a side effect in glaucoma patients using calcium channel blockers for systemic hypertension. However, prescribing therapeutic doses of calcium channel blockers to non-hypertensive glaucoma patients subjects the optic nerve to a risk of hypoxia secondary to iatrogenic hypotension and severely disrupts inherent transmembrane calcium modulation.

Ocular Vascular Disease

In the optic nerve two tissues are particularly vulnerable to hypoxia:
  a. The microglial ganglion cells.
  b. The transiting axonic neurons.

A reduction in optic nerve oxygen delivery may follow acute or chronic, segmental or widespread, vascular spasm or prolonged constriction secondary to a physical reduction in the vascular lumen. This luminal reduction (vasoconstriction) may be caused by or associated with hypertrophy of the vascular muscle wall (the media), the accumulation of atherosclerotic plaque, platelet agglutination and/or local inflammatory swelling and leukocytic accumulation. Any and all of these findings may occur with aging and with systemic disease: diabetes, hypertension, dyslipogenesis, arteriosclerosis, thyroid disease, etc. Although vascular insufficiency at specific tissue sites is widely variable and not predictable with certainty, the fact that most glaucoma patients are over 50 years old makes the frequency of these risk factors and the frequency of vascular insufficiency high in this clinical group.

If a reduction of optic nerve vascular risk factors is united with a reduction in outflow resistance, the combined effects of a more pressure resistant nerve head and lower IOP will beneficially decrease the potential for optic atrophy and blindness.

Glaucoma—Present Treatment

Current non-surgical treatments of COAG are based upon a limited number of biochemical approaches and focus exclusively upon reducing IOP:

a. Enzyme poisons—these are most frequently tablets of carbonic anhydrase inhibitors that inhibit the production of aqueous humor. Besides the development of renal stones, potassium loss is a constant clinical concern. Topical forms of this group have appeared as eye drops. However, because carbonic anhydrase activity is also present in the cytoplasm of corneal endothelial cells the long-term corneal effects of this form of these medications are unknown. To avoid systemic reactions, patients with sulfonamide allergies should not use these drugs.

b. Parasympathomimetics—pilocarpine-containing eye drops are widely prescribed and act by causing pupillary constriction. Miosis causes lacunae in the trabeculum to enlarge; thus, mechanical resistance to aqueous outflow is reduced. Frequent side effects include headache from iris spasm, decreased night vision from miosis and blurred vision, especially in myopes.

c. Beta blocking agents—these drugs block the beta-adrenergic sympathetic rete responsible for increased vascular flow to the ciliary processes and reduce the production of aqueous humor. They also increase aqueous outflow through the trabeculum. These agents must be used with great caution in patients with low blood pressure (orthostatic hypotension), sinus bradycardia or second/third degree heart block (severe bradycardia), obstructive pulmonary disease or bronchial asthma (acute bronchospasm) and diabetes (masking of hypoglycemia). They result in impotency in a significant number of men. There is contested evidence that some ocular beta blocking agents generally reduce blood flow to the posterior segment of the eye.

d. Topical prostaglandin analogs—this new group of anti-inflammatory eye drops presumably reduces IOP by widening the inter-trabecular space and, perhaps, by reducing trabecular platelet aggregation. Their use is associated with progressive and possibly permanent change in iris color to brown and some embryocidal outcomes in labroatory animals. Women of reproductive age and nursing women should avoid their use.

All of these treatment modes have significant and unavoidable, potential or demonstrable, local or systemic side effects or toxicities that directly contraindicate their use, reduce patient compliance or are worrisomely interactive with other systemic pharmaceuticals.

B. Non-Insulin-Dependent Diabetes Mellitus (NIDDM)

Non-insulin-dependent diabetes is prevalent in up to 35% of the population. It is most frequently a disorder of middle and later life. It is both part of the aging process and a process that advances aging. Diabetes affects metabolism in totality: carbohydrate, lipid and protein.

There are two clinical forms of diabetes, each with a different pathogenesis: Type 1, insulin-dependent diabetes mellitus (IDDM) and Type 2, non-insulin-dependent diabetes mellitus (NIDDM). NIDDM represents 90% of all diabetics. In NIDDM, cellular resistance to the effectiveness of insulin results in above normal levels of insulin secretion. When this compensatory increase of insulin production cannot be maintained and/or when insulin resistance increases further, blood sugar rises, lipid and protein metabolism are disturbed and the insidious processes of vascular complications of long-term diabetes begin.

Diabetes is characterized by a congeries of pathologies other than hyperglycemia; most seriously, patients develop specific microvascular and non-specific macrovascular complications including retinopathy, nephropathy, neuropathy and frequently severe atherosclerosis affecting, among others, the coronary, cerebral and peripheral vascular trees. Causative mechanisms of these complications include free radical damage, non-enzymatic protein glycation, lipoprotein disturbances and disorders of sorbitol and myoinositol metabolism.

Insulin resistance with secondary hyperinsulinemia and/or hyperglycemia disturbs several physiological conditions and functions and, thus, contributes to many disorders associated with aging, e.g., hypertension, obesity, atherosclerosis, lipid abnormalities and chronic metabolic perturbations including fully developed NIDDM.

In diabetes, as in aging, elevated circulating glucose reacts non-enzymatically with proteins and nucleic acids to form products that: 1) disturb the functionality of the cellular phospholipid membrane, 2) diminish tissue elasticity and 3) increase lipid peroxidation.

Disturbances in glucose/insulin metabolism are associated with greatly increased lipid peroxidation from elevated free radical formation resulting from the auto-oxidation of glucose. This augmented free radical formation and lipid peroxidation are associated with the "premature aging" of diabetic patients.

Ingestion of sugars, fats and sodium have been linked to decreased insulin sensitivity, while caloric restriction, exercise, ingestion of chromium, vanadium, magnesium, and certain antioxidants have been associated with greater insulin sensitivity. Thus, manipulation of the diet by influencing the glucose/insulin system may favorably affect lifespan and reduce the incidence of the microvascular and macrovascular complications of NIDDM.

The earliest microvascular lesion of diabetes is thickening of the basement membrane. A healthy basement membrane provides stability and a permeability barrier. Cellular impermeability requires a negative electrical charge provided by heparan sulfate, a proteoglycan. Sulfate groups provided by thiol contributors like α-lipoic acid and N-acetylcysteine (NAC) may contribute to the adequacy of this necessary negativity of the cell membrane. In diabetes both the basement membrane thickness and heparan sulfate levels are decreased, as is overall membrane sulphonation. As a result, vessel permeability is increased. Increased vessel permeability is the most notable initial microvascular complication in diabetes.

Although arteriolar and capillary microvascular intraluminal pressure and flow may be increased, laminar flow is disordered by clumping of cellular elements. These disturbances, plus the increased permeability of the basement membrane and associated vascular endothelial dysfunction, limit normally efficient vascular autoregulatory mechanisms, and the latter eventually leads to clinically apparent microvascular and macrovascular insufficiencies of the legs, feet, heart, eye and brain.

NIDDM—Present Treatment

Current pharmacological approaches focus upon improving glucose homeostasis, but frequently do not succeed in permanently restoring normoglycemia in most patients.

For glycemic regulation, four classes of drugs are currently available: sulphonylureas, biguanides, alpha-glucosidase inhibitors and insulin. Adjunct treatments may help to improve glycemic control by correcting selected abnormalities associated with NIDDM, such as obesity and hyperlipidemia.

C. Vasoconstriction

Vasoconstriction, or a reduction in the cross-sectional area of the lumen of blood vessels, is due either to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus among others.

Vasoconstriction originates in a variety of ways. One example is the local conversion of circulating low density lipoproteins (LDL) into oxidatively activated low density lipoproteins (oxLDL), which are internalized via cellular macrophage scavenger receptors called "foam cells". These cells are bound to the vascular endothelium, release cytokines and trigger local expression of leukocyte adhesion molecules.

Another example is the unopposed endothelial cell release of the vasoconstrictor, ET-1. Prolonged vasospasm results in proliferation of vascular smooth muscle cells (VSMC) and a mechanical reduction of luminal cross-section. In particular, oxLDL and hyperlipidemia impair endothelial-dependent vascular relaxation because of the inhibition of histamine-stimulated release of NO from endothelial cells. This induces a sometimes-inadequate adaptive increase in the level of intracellular glutathione (GSH) in VSMC.

A third example is the free radical-stimulated activation, local accumulation, and adhesion of platelets and white blood cells on the endothelial surface which produce chemoattractants for macrophages that eventually will be converted into "foam cells".

A fourth example is the irregular vasoconstriction or vascular aneurismal pouching due to the death of perivascular pericytes caused by the conversion of glucose to sorbitol in diabetes mellitus.

Vasoconstriction and atherogenesis can be modulated by a number of mechanisms: inhibition of LDL oxidation by α-tocopherol (vitamin E) and ascorbate (vitamin C); limitation of the production of ROS and, thus, cell-mediated LDL oxidation; reduction of adhesion molecule expression and monocyte recruitment; protection for the release of NO and reduction in the proliferation of VSMC, etc. Many, if not most, of these processes are regulated by nuclear factor-kappa B or related transcription factors that are redox-sensitive and capable of modification by antioxidants. Furthermore, antioxidants directly limit the cytotoxic effects of oxLDL and thereby reduce vascular cell necrosis and lesion progression.

II. Biofactors and Biochemistry

The main oxidizing free radicals are oxygen-derived metabolites, such as: superoxide anion (O.), hydrogen peroxide ($H_2O_2$), hydroxyl radical ($OH^-$), hypochlorous acid (HOCl), chloramines ($NH_2Cl$), nitrogen oxides (NO.), ozone ($O_3$) and lipid peroxides. They are produced continually by living organisms, either in the intracellular compartment by the mitochondrial respiratory chain and mixed function oxidase system, or in the extracellular compartment, especially by phagocytes. The body possesses complex protective antioxidant systems against this potentially toxic environment. These systems include dismutase superoxides, catalases, metallic ion sequestration, enzymes which degrade proteins damaged by free radicals, metabolizing hydroperoxides, inherent DNA repair processes, and in particular, the GSH enzyme system. A physiological steady state is established during healthy, normal conditions between the production of oxidants and their neutralization by antioxidants.

A. Glutathione

Human GSH (gamma-glutamyl-cysteinyl-glycine) levels cannot be raised directly by supplemental administration in the diet. GSH is produced inside the cell from the amino acids glutamic acid, cysteine and glycine and acts as a cofactor for protective enzymes such as selenium-dependent glutathione peroxidase (GSHPx). Zinc is a necessary trace element in its synthesis. GSH presence in the brain is enhanced by pineal melatonin via this neurohormone's ability to increase the mRNA of GSHPx.

Reduced GSH is important and ubiquitous. It is necessary for intracellular transduction signaling, for the modulation of cellular apoptosis and necrosis, and the modulation of red blood cell fragility. During its function as an antioxidant it is oxidized to disulfide glutathione (GSSG). This action importantly protects vascular endothelium from free radical damage. GSH inhibits the peroxidation of LDL directly reducing atherosclerotic and vasoconstrictive risks, and oxLDL-induced mitochondrial DNA mutations. Besides their influence upon atherogenesis and vasoconstriction, these effects are linked to a variety of specific sensory neuropathies.

GSH and Neurodegenerative Diseases

GSH plays multiple roles in the nervous system including free radical scavenging, redox modulation of ionotropic receptor activity and neurotransmission. GSH depletion enhances oxidative stress and increases the level of neuroexcitotoxic molecules; in distinct neuronal populations both of these events can initiate cell death. Evidence for the dual roles of oxidative stress and diminished neural GSH status is present in Lou Gehrig's disease (ALS), Parkinson's disease and Alzheimer's disease.

Exposure to glutamate, a critical neurotransmitter, causes depletion of intracellular mitochondrial GSH leading to the accumulation of ROS and, ultimately, neural apoptosis. Cells that have enhanced rates of GSH regeneration—due to higher activities of the GSH metabolic enzymes gamma-glutamylcysteine synthetase and GSH reductase—appear to be resistant to glutamate-induced ROS.

Neurodegenerative disorders occurring with age, e.g. Alzheimer's disease and prion-based diseases like Creutzfeldt-Jakob disease are associated with a reduction of GSH levels. Normalization of the GSH level appears to exert a neuroprotective effect.

(Also see GSH relationship with CNS metallothioneins, below)

GSH and Aging

GSHPx levels appear to rise with aging; this may reflect a physiological attempt to provide compensatory increases in the GSH needed to counter the rising levels of ROS associated with increasing age.

Because the protection of the electron acceptor homocysteine thiolactone declines with aging, homocysteine levels frequently increase. GSH levels are lowered by homocysteine.

GSH is low in the presence of hypomagnesemia. Hypomagnesemia is commonly present in the aging (and the diabetic) population.

GSH increases the oxidative stability of muscle tissue and presumably improves aging muscular tone.

GSH and Diabetes

The elevated oxidative stresses associated with hyperglycemia may be involved in the abnormal activation of the coagulation cascade found in diabetics. Prothrombin fragment 1+2 (F1+2) represents a reliable marker of the amount of thrombin released. During oral glucose tolerance tests, F1+2 significantly increases in both diabetic and healthy subjects. Intravenous GSH administration during these tests normalizes this phenomenon and significantly decreases F1+2 in diabetics.

Reduced GSH is a cofactor for the glyoxalase system, a metabolic pathway that catalyses the detoxification of α-oxoaldehydes (RCOCHO) to corresponding aldonic acids ($RCH(OH)CO_2H$). This detoxification protects cells from α-oxoaldehyde-mediated formation of advanced glycation endproducts (AGEs). AGEs are implicated in a wide variety of diabetic vascular abnormalities and, perhaps, in the pathogenesis of macular degeneration.

Polyol-(sorbitol) induced decreases in nicotinamide adenine dinucleotide phosphate (NADPH) in erythrocytes from patients with NIDDM impair the redox status of GSH. Since activation of the polyol pathway is significant in diabetes, decreases in NADPH and GSH levels occur.

Retinal gamma-glutamyl transpeptidase (GTT) activity and GSH levels are significantly reduced in diabetic and galactosemic rats. Consumption of the antioxidants ascorbic acid plus α-tocopherol inhibits these decreases of retinal GTT activity and GSH levels. This suggests that defects in GSH regulation in the diabetic retina are secondary to hyperglycemia-induced oxidative stress.

A significantly lower content of sulfhydryl proteins is present in the lens and vitreous of diabetic patients. This is associated with an increased formation of protein-bound free sulfhydryls, one index of oxidative damage to proteins. In addition, GSHPx activity is decreased in the lenses of diabetic patients. Presumably this would result in reduced levels of GSH in the diabetic lens.

Free radicals have been proposed as fundamental to the development of diabetic retinopathy because they are routinely produced in high volume by the abnormal metabolism of diabetes. Microvascular ischemia/reperfusion cycles, which interfere with the FR enzyme defense system of the retina, i.e., with GSH, are also implicated.

GSH and the Eye

The ciliary body in particular appears to contain an inducible and very active mono-oxygenase system prone to ROS generation. These ROS, combined with those produced via the cyclo-oxygenase pathway probably result in damage through oxidative stress-mediated vascular constriction.

In the retina the photoreceptor rhodopsin itself may be the photodynamic agent that initiates ROS formation. High concentrations of retinal polyunsaturated fatty acids (PUFAs) in the photoreceptor membranes form additional ROS by auto-oxidation.

Fatty acids, e.g., C22:6 omega 3, are especially concentrated in rods and cones and in the phosphatidyl ethanolamine of retinal synaptosomes. As a result of peroxidation, malondialdehyde is formed. This aldehyde appears to cross-link the amino groups of proteins with phospholipids, which results in the production of retinal lipofuscin. From this source drusen are formed. The latter are precursors of senile macular degeneration—a major source of visual disability in the aging population.

The protective antioxidative capacity of the youthful and healthy ciliary body is correspondingly very high (especially via SOD and GSH). Toxic peroxidation processes in particular are countered by these enzyme systems and antioxidants. However, rapid oxidation of ascorbate in the aqueous yields $H_2O_2$, which itself is locally toxic to endothelial cells. A potentially important, relationship may exist between unmodulated aqueous increases of $H_2O_2$ and $H_2O_2$-derived toxic ROS (e.g., $OH^+$), and the development of various ocular pathologies such as glaucoma, cataract, macular degeneration and retinal vascular damage, including the neovascularization of prematurity. This oxidation of ascorbate in the aqueous humor is limited by GSH.

GSH and Vasoconstriction

Redox-sensitive mechanisms are involved in VSMC growth. ROS that promote VSMC growth are inhibited by GSH. This is not surprising since, upon oxidation, micronutrients need to be regenerated in the biological setting, hence their need for coupling to complex, often redundant, nonradical-reducing systems such as GSH/GSSH or NADPHINADP+ and NADHINAD+. For example: the water-soluble, antioxidant vitamin C can reduce oxidized vitamin E tocopheroxyl radicals directly or indirectly; however, other reducing compounds such as α-lipoic acid and GSH can also perform these functions.

An inverse correlation exists between the extent of macrophage-mediated oxidation of LDL and cellular GSH content. Supplemental thiols which increase GSH levels should protect endothelial cells from atherosclerotic damage, perturbations of laminar flow, VSMC hypertrophy, cell detachment, et al, and thus help to preserve a normal NO/ET-1 ratio.

However, some details of the protective functions of GSH function remain unclear. Electrophoretic mobility shift assays demonstrate that activation of oxLDL and tumor necrosis factor alpha (TNF alpha) is not attenuated by GSH or by cGMP analogues.

B. GSH Thiol Contributors a. Cysteine

Cysteine is a necessary thiol precursor of GSH. Cysteine is a powerful scavenger of peroxynitrite, an extremely toxic free radical that is responsible for DNA damage, decreases in mitochondrial respiration and the loss of cellular levels of NAD+ [69]. Additionally cysteine reduces arachidonic acid release, prostaglandin E2 synthesis and lipid peroxidation, all events associated with inflammatory states.

b. N-acetyl L-cysteine (NAC)

As mentioned above, oxLDL induces apoptosis in human macrophages, a significant feature of atherogenesis. However, cell cultures exposed to NAC before they are exposed to oxLDL, TNF-alpha or $H_2O_2$, do not experience decreases in cellular GSH concentrations. This is especially true in apoptotic macrophages present in human atherosclerotic plaques. NAC has a GSH sparing effect under these circumstances.

In another supporting study, NAC inhibited inflammatory interleukin (IL-8) expression induced by TNF-alpha. Such local inflammatory elements are increasingly implicated in vascular atherosclerotic changes associated with cardiac disease.

c. L-2-oxothiazolidine-4-carboxylate (OTC)

Cellular oxygenases and antioxidants, including GSH, modulate macrophage-mediated oxidation of LDL in early atherogenesis. OTC delivers cysteine residues to the cells for GSH synthesis. Supplementation with OTC (and selenium which increases cellular GSH synthesis) seems to increase macrophage GSH content and GSHPx activity. OTC should reduce cellular oxLDL production.

Increased vascular oxidative stress impairs the effective vasorelaxation action of NO in atherosclerosis. NO action is improved by the administration of ascorbic acid (which regulates intracellular redox states) perhaps by sparing cellular GSH. By providing substrate cysteine for GSH synthesis and thus augmenting intracellular GSH, OTC improves NO-dependent, flow-mediated dilatation. At the same time OTC has no effect on direct arterial dilation caused by nitroglycerin or upon systemic blood pressure, heart rate, or reactive hyperemia.

d. N-(2-Mercaptopropionyl)glycine (MPG)

MPG is a reducing, radical scavenging, antioxidant agent that decreases hydroxyl concentration and the hypoxic induction of mRNA. Other studies have shown that MPG also prevents the reduction of tyrosine hydroxylase mRNA by $H_2O_2$.

Antioxidants are known to mitigate the cardiac contractile dysfunction that follows brief periods of ischemia ("myocardial stunning"); following such ischemia, both re-flow and isovolumic pressures recovered completely in a MPG treated group.

Studies have been made of the presumably antioxidant radioprotective effects of MPG upon the cells of bone marrow in irradiated mice. MPG pre-treatment of the mice resulted in a significant reduction in the percentage of aberrant metaphases.

C. Magnesium ($Mg^{+2}$)

Although the recommended daily allowance of ionic $Mg^{+2}$ for humans is 350 mg. $Mg^{+2}$ deficiencies have been documented in many segments of the world population. The average adult in Western society has a dietary $Mg^{+2}$ shortfall of 90–178 mg. per day. $Mg^{+2}$ deficiencies are particularly prevalent among diabetics with normal renal function, alcoholics, smokers, the elderly, and those who suffer from a variety of gastrointestinal mobility disorders.

Ionic $Mg^{+2}$ in mammals resides in three compartments: (1) in bone; (2) in an intracellular bound form or in an intracellular unbound form; and (3) in circulating bound and unbound forms. When the concentration of circulating $Mg^{+2}$ in the bloodstream increases as a result of dietary uptake of $Mg^{+2}$, the body responds by attempting to sequester the $Mg^{+2}$ into one of the bound or intracellular forms listed above. However, if elemental $Mg^{+2}$ is rapidly ingested in a bulk amount that results in the absorption of a $Mg^{+2}$ bolus in excess of 8 mEq, the renal excretion of $Mg^{+2}$ quickly increases and becomes less efficient in the resorption of this element. Thus the accurate sustenance of an appropriate $Mg^{+2}$ level requires the repeated administration of carefully designed medicaments with correctly formulated, targeted amounts.

$Mg^{+2}$ deficiencies impair antioxidant defenses through decreased synthesis of GSH and a reduced activity of CuZnSOD. $Mg^{+2}$ deficiencies enhance general oxidative stress levels by raising circulating levels of factors that promote free radical generation and which are mitogenic. This may result in increased tissue necrosis in the presence of acute local levels of active oxygen species or hydroxyl radicals.

D. Copper ($Cu+^2$)

$Cu^{+2}$ is an essential trace element required for a number of enzymes that are necessary for normal metabolic function. Metabolic balance studies have demonstrated that daily $Cu^{+2}$ losses are approximately 1.3 mg/day. In order to remain in $Cu^{+2}$ balance, the average adult male must consume a diet that contains at least 2 mg copper/day. It has been assumed that most diets satisfy this requirement because of the ubiquitous presence of $Cu^{+2}$ in most foodstuffs. Recent studies, however, have shown that dietary $Cu^{+2}$ may often fall below the estimated daily needs.

The essential yet toxic nature of $Cu^{+2}$ demands tight regulation of the $Cu^{+2}$ homeostatic machinery to ensure that sufficient $Cu^{+2}$ is present in the cell to drive essential biochemical processes yet prevent accumulation to toxic levels.

The results of some studies demonstrate that $Cu^{+2}$ deficiency results in alterations of the regulatory mechanisms governing inflammation and thrombosis.

$Cu^{+2}$ is strongly involved in the synthesis of GSH and is necessary for the activity of the antioxidant CuZnSOD.

E. Zinc ($Zn^{+2}$)

Compared with controls, rats fed a $Zn^{+2}$-deficient diet without supplementary antioxidants have greater red blood cell osmotic fragility, higher concentrations of thiobarbituric acid-reactive substances (TBARS), higher GSHS-transferase activity, lower concentration of GSH and of GSHPx, as well as lower activity of CuZnSOD. High dietary levels of $Zn^{+2}$ appear to reduce levels of CuZnSOD. In one study there was no relationship between serum $Zn^{+2}$ levels and CuZnSOD activity or the serum concentration of GSHPx activity in a group of healthy subjects. However, in elderly subjects given $Zn^{+2}$ supplements for one year, mean plasma levels of α-tocopherol, vitamin C and $Cu^{+2}$ increased significantly after 6 months of supplementation. A significant increase in GSHPx levels was observed in patients receiving these trace elements alone or in association with vitamins.

$Zn^{+2}$ binds the sulfhydryl groups in proteins, protecting them from oxidation. $Zn^{+2}$ status does not directly control tissue peroxide levels but can protect specific molecules against oxidative and peroxidative damage.

Many areas of the brain contain high contents of $Zn^{+2}$: the retina, the pineal gland (note relationship to the pineal antioxidant, melatonin) and the hippocampus all synthesize unique metallothioneins (MT) on a continuous basis. MT are $Zn^{+2}$-binding proteins consisting of 25–30% cysteine. GSH may participate in releasing $Zn^{+2}$ from MT. The concentration of $Zn^{+2}$ is altered in a number of disorders of the central nervous system: alcoholism, Alzheimer's dementia, Down syndrome, epilepsy, Friedreich's ataxia, Guillaine-Barré syndrome, hepatic encephalopathy, multiple sclerosis, Parkinson's disease, Pick's disease, retinitis pigmentosa, retinal dystrophy, schizophrenia, and Wernicke-Korsakoff syndrome.

SUMMARY OF THE INVENTION

The invention resides in the synthesis and application of unique, efficient molecules presented in dosage forms clinically useful as nutritional supplements for, among others, chronic glaucoma, diabetes, macular degeneration, neurodegenerative diseases and vasoconstriction. It introduces a variety of molecules unique in design and/or in application.

1. Metal thiol complexes included in this invention have the following formula

[A]M X wherein
 a. A is L-cysteine, NAC, OTC or MPG,
 b. M is $Mg^{+2}$, $Cu^{+2}$, $Zn^{+2}$ or $Se^{+2}$,
 c. X is hydroxide, halide, acetate or ascorbate, prepared in oral unit dosage forms clinically useful for chronic glaucoma, NIDDM, macular degeneration, neurodegenerative diseases or vasoconstriction, among others.

2. Additional metal thiol complexes included in this invention have the following formula $[A]_2MX$ wherein a. $[A]_2$ is bis-L-cysteine, bis-NAC, bis-OTC or bis-MPG,
b. M is $Mg^{+2}$, $Cu^{+2}$, $Zn^{+2}$ or $Se^{+2}$,
c. X is hydroxide, halide, acetate or ascorbate, prepared in oral unit dosage forms clinically useful for chronic glaucoma, NIDDM, macular degeneration, neurodegenerative diseases or vasoconstriction, among others.

3. Non-metal containing thiol complexes included in this invention have the following formula $[A]X$ wherein a. A is L-cysteine, NAC, OTC or MPG,
b. X is hydroxide, halide, acetate, ascorbate or bis-ascorbate, prepared in oral unit dosage forms clinically useful for the alteration of conditions and functions associated with aging, chronic glaucoma, NIDDM, macular degeneration, neurodegenerative diseases and vasoconstriction.

4. Additional non-metal containing thiol complexes included in this invention have the following formula $[A]_2X$ wherein a. $[A]_2$ is bis-L-cysteine, bis-NAC, bis-OTC or bis-MPG,
b. X is hydroxide, halide, acetate, ascorbate or bis-ascorbate, prepared in oral unit dosage forms clinically useful for the alteration of conditions and functions associated with aging, chronic glaucoma, NIDDM, macular degeneration, neurodegenerative diseases and vasoconstriction.

Processes for the Synthesis of Salts:

The magnesium and zinc salts of N-acetyl-L-cysteine and L-cysteine are prepared as described in U.S. Pat. Nos. 3,647,834 and 3,749,770 by treating 2 molar equiv. of the carboxylic acids with one molar equiv. of the carbonate salts of magnesium and zinc respectively. The magnesium and zinc salts of L-2-oxothiazolidine-4-carboxyoic acid and N-(2-mercaptopropionyl)glycine are prepared in a similar manner. Alternatively, the magnesium salts are prepared by treating 2 molar equiv. of the carboxylic acid with 1 molar equiv. of magnesium ethoxide. In the foregoing preparations, replacement of one molar equiv. of acid with one molar equiv. of ascorbic acid gives the salt of the acid and ascorbic acid in a 1:1 molar ratio. The copper salts of L-cysteine, N-acetyl-L-cysteine and L-2-oxothiazolidine-4-carboxyoic acid are prepared according to the method described in U.S. Pat. No. 4,089,969 and J. Amer. Chem. Soc. 82,4174 (1960) whereby the corresponding potassium salts (2 molar equiv.) of these acids are treated with one molar equivalent of cupric nitrate. Alternatively, the copper salts are prepared by treatment of the acid, e.g., N-(2-mercaptopropionyl)glycine, with an alcoholic solution of cupric acetate as descried in J. Chem. Soc.2545 (1957). The salts of other mixed acids, wherein the counter ion is acetate, chloride and hydroxide are also included in this invention. These salts are prepared by conventional methods that are disclosed in the Examples section below.

SYNTHESIS PROCESSES

EXAMPLE 1

Magnesium bis-N-Acetyl-L-cysteinate—Mg$(C_5H_8NO_3S)_2$

To a stirred suspension of 16.3 g of N-Acetyl-L-cysteine (Aldrich Chemicals) in 200 ml of water was added 5 g of magnesium carbonate. The reaction mixture was stirred at 40–50° C. until the evolution of carbon dioxide ceased and then filtered. The collected solids were washed with 2×100 ml of water and combined filtrates were evaporated to dryness under reduced pressure to yield 17 g of the magnesium salt as a white solid.

EXAMPLE 2

Zinc bis-N-Acetyl-L-cysteinate—Zn$(C_5H_8NO_3S)_2$

To a stirred suspension of 32.6 g of N-Acetyl-L-cysteine in 300 ml of water was added 13.8 g of powdered zinc carbonate. The reaction mixture was stirred at 40–50° C. until the evolution of carbon dioxide ceased and then filtered. The collected solids were washed with 2×100 ml of water and combined filtrates were evaporated to dryness under reduced pressure to yield 38 g of the zinc salt as a solid.

EXAMPLE 3

Copper bis-N-Acetyl-L-cysteinate—Cu$(C_5H_8NO_3S)_2$

To a suspension of 32.6 g of N-Acetyl-L-cysteine in 150 ml of water was added a solution 11.2 g of potassium hydroxide in 50 ml of water. The reaction mixture was stirred with cooling (ice bath) in a nitrogen atmosphere until a clear solution was obtained. A solution of 24.2 g of cupric nitrate trihydrate in 100 ml was added and stirring was continued until precipitation of the copper salt was complete. The precipitate was then collected by filtration, washed with cold water and vacuum-dried at room temperature to yield copper salt as a pale blue solid.

EXAMPLE 4

Magnesium bis-L-cysteinate—Mg$(C_3H_6NO_2S)_2$

L-cysteine (24 g) (Aldrich Chemicals) was dissolved in 250 ml of absolute ethanol and the resulting solution was treated with a solution of 11.4 g of magnesium ethoxide (Aldrich Chemicals) dissolved in 100 ml of absolute ethanol. This solution was kept in a nitrogen atmosphere for 1 hr and then the solvent was evaporated under reduced pressure to yield 26 g of the magnesium salt.

EXAMPLE 5

Zinc bis-L-cysteinate—Zn$(C_3H_6NO_2S)_2$

L-cysteine (24.2 g) was dissolved in 200 ml of stirred water and 13.8 g of powdered zinc carbonate was added to the stirred solution. This mixture was then stirred at 40–50° C. until the evolution of carbon dioxide ceased. The reaction mixture was worked up as described in Example 1 to yield 26 g of the zinc salt as a solid.

EXAMPLE 6

Copper bis-L-cysteinate—Cu$(C_3H_6NO_2S)_2$

To a solution of 24.2 g of L-cysteine in 150 ml of water was added a solution of 11.2 g of potassium hydroxide in 50 ml of water in a nitrogen atmosphere. A solution of 24.2 g of cupric nitrate trihydrate in 100 ml of water was then added and the resulting solution was stirred until precipitation of the copper salt was complete. The precipitate of copper bis-cysteinate was collected by filtration, washed with cold water and vacuum-dried at room temperature.

EXAMPLE 7

Magnesium bis-L-2-Oxothiazolidine-4-Carboxylate—Mg($C_4H_4NO_3S$)$_2$

L-2-Oxothiazolidine-4-carboxylate (29.2 g) (Aldrich Chemicals) was dissolved in 250 ml of absolute ethanol and the resulting solution was treated with a solution of 11.4 g of magnesium ethoxide dissolved in 100 ml of absolute ethanol. The solution was kept for 1 hr in a nitrogen atmosphere and the solvent was then evaporated under reduced pressure to yield 31 g of the magnesium salt as a solid.

EXAMPLE 8

Zinc bis-L-Oxothiazolidine-4-Carboxylate—Zn ($C_4H_4NO_3S$)$_2$

To a stirred solution of L-2-oxothiazolidine-4-carboxylate (29.4 g) in 400 ml of ethanol-water (1:4) was added 13.8 g of powdered zinc carbonate. The reaction mixture was stirred at 40–50° C. until the evolution of carbon dioxide ceased and then worked up as described in Example 1 to yield 35 g of the zinc salt as a solid.

EXAMPLE 9

Copper bis-L-2-Oxothiazolidine-4-Carboxylate—Cu ($C_4H_4NO_3S$)$_2$

A suspension of 29.4 g of L-2-oxothiazolidine-4-carboxylate in 400 ml of ethanol-water (1:4) was treated with a solution of 11.2 g of potassium hydroxide in 50 ml of water and the mixture was stirred until a clear solution resulted. A solution of 24.2 g of cupric nitrate trihydrate in 100 ml of water was added and stirring was continued until the precipitation of the copper salt was complete. After being cooled in an ice bath, the precipitate of copper bis-L-oxothiazolidine-4-carboxylate was collected by filtration, washed with cold water and vacuum-dried at room temperature to yield 35 g.

EXAMPLE 10

Magnesium bis-N-(2-Mercaptopropionyl)-Glycinate—Mg($C_5H_8NO_3S$)$_2$

N-(2-Mercaptopropionyl)-glycine (32.6 g) (Aldrich Chemicals) was dissolved in 400 ml of absolute ethanol and the resulting solution was treated with a solution of 11.4 g of magnesium ethoxide in 100 of absolute ethanol. This solution was kept in a nitrogen atmosphere for 1 hr and then the solvent was evaporated under reduced pressure to yield 34 g of the magnesium salt as a white solid.

EXAMPLE 11

Zinc bis-N-(2-Mercaptopropionyl)-Glycinate—Zn ($C_5H_8NO_3S$)$_2$

To a stirred suspension of 32.4 g of N-(2-mercaptopropionyl)-glycine in 500 ml of ethanol-water (1:1) was added 13.8 g of powdered zinc carbonate in a nitrogen atmosphere. The reaction mixture was then stirred overnight after which time the alcohol and water were evaporated under reduced pressure at 50° C. to afford a residue of the zinc salt of 38 g.

EXAMPLE 12

Copper bis-N-(2-Mercaptopropionyl)-Glycinate—Cu($C_5H_8NO_3S$)$_2$

A solution of 1.8 g of cupric acetate in 50 ml of ethanol was added to a stirred solution of 3.3 g of N-(2-mercaptopropionyl)-glycine in 100 ml of ethanol. The solvent and the formed acetic acid were removed by evaporation in high vacuum (0.01 mm). This yielded 3.8 g of the copper salt of bis-N-(2-Mercaptopropionyl)-glycine.

EXAMPLE 13

Magnesium N-Acetyl-L-cysteinate-L-Ascorbate—Mg($C_5H_8NO_3S$).($C_6H_7O_6$)

To a stirred suspension of 16.3 g of N-acetyl-L-cysteine and 17.6 g of L-ascorbic acid in 400 of water was added 8.4 g of powdered magnesium carbonate. The mixture was stirred at 40–50° C. until the evolution of carbon dioxide ceased. The reaction mixture was then cooled, filtered and the collected solids were washed with 2×100 ml of water. The combined filtrates were evaporated to dryness under reduced pressure to yield 36 g of the magnesium salt.

EXAMPLE 14

Zinc N-Acetyl-L-cysteinate Ascorbate—Zn ($C_5H_8NO_3S$).($C_6H_7O_6$)

To a stirred suspension of 16.3 g of N-acetyl-L-cysteine and 12.5 g of zinc carbonate in 400 ml of water was added 6 g of acetic acid. This mixture was stirred at 40–50° C. until the evolution of carbon dioxide ceased. The reaction mixture was cooled, filtered and the residue washed with 2×100 ml of water. The combined filtrates were evaporated to dryness under reduced pressure to yield 28 g of the zinc salt.

EXAMPLE 15

Magnesium L-Cysteinate-L-Ascorbate—Mg ($C_3H_6NO_2S$).($C_6H_7O_6$)

To a stirred suspension of 12.1 g of L-cysteine and 17.6 g of L-ascorbate in 400 ml of water was added 8.4 g of powdered magnesium carbonate. The reaction mixture was stirred at 40–50° C. until the evolution of carbon dioxide ceased and then processed according to the procedure described in example 13. This gave 32 g of the solid magnesium salt.

EXAMPLE 16

Copper L-2-Oxothiazolidine-4-carboxylate Acetate—Cu($C_4H_4NO_3S$).($C_2H_3O_2$)

A solution of 14.7 g of L-oxothiazolidine-4-carboxylate Acid and 18.2 g of cupric acetate in 500 ml of ethanol was stirred in a nitrogen atmosphere for 1 hr. The solvent was evaporated under reduced pressure and the residual acetic acid was removed by heating the residue at 40–50° C. in high vacuum (0.01 mm) for several hours. This gave 26 g of the copper salt as a pale blue powder.

EXAMPLE 17

Copper L-2-Oxothiazolidine-4-carboxylate Chloride—Cu($C_4H_4NO_3S$).Cl

By following the procedure of example 16 and replacing cupric acetate by cupric chloride, there was obtained copper L-oxothiazolidine-4-carboxylate chloride.

EXAMPLE 18

Magnesium L-2-Oxothiazolidine-4-carboxylate Acetate—$Mg(C_4H_4NO_3S) \cdot (C_2H_3O_2)$ To a stirred suspension on 14.7 g of L-oxothiazolidine-4-carboxylate acid and 8.4 g of magnesium carbonate in 400 ml of water was added 6 ml of acetic acid. This mixture was stirred at 40–50° C. until the evolution of carbon dioxide ceased and then processed according to the procedure described in example 13. This gave 22 g of the solid magnesium salt.

EXAMPLE 19

Zinc N-(2-Mercaptopropionyl)-glycine-L-Ascorbate—$Zn(C_5H_8NO_3S) \cdot (C_6H_7O_6)$ To a stirred suspension of 15.3 g of N-(2-mercaptopropionyl)-glycine and 17.6 g of L-ascorbic acid in 500 ml of ethanol-water (1:1) was added 12.5 g of powdered zinc carbonate. The reaction mixture was stirred at 40–50° C. until the evolution of carbon dioxide ceased and then processed according to the procedure described in example 13. This gave 40 g of the zinc salt as a white solid.

EXAMPLE 20

Magnesium L-2-Oxothiazolidine-4-carboxylate Hydroxide—$Mg(C_4H_4NO_3S) \cdot (OH)$ L-2-Oxothiazolidine-4-carboxylic acid (1.5) was dissolved in 25 ml of absolute ethanol and a solution of 1.2 g of magnesium ethoxide in 10 ml of absolute ethanol was added after 10 min, 3 ml of water was added and the ethanol was evaporated under reduced pressure. The excess water was removed by heating the residue at 40–50° C. in high vacuum (0.01 mm) for several hours. This gave 1.8 g of magnesium L-2-oxothiazolidine-4-carboxylate hydroxide as a white solid.

GSH is a critically important antioxidant whose intracellular level must be maintained. These levels especially must be sustained at a high level in glaucoma, diabetes, macular degeneration and vasoconstriction. This invention provides dosage forms of metal salts and thiol contributors to ensure that appropriate levels of both GSH and metallic biofactors that act in a complementary way are maintained in these clinical conditions.

Because GSH cannot be directly administered as a supplement in the human diet, the invention defines thiol containing molecules that effectively will maintain in these clinical conditions appropriate clinical levels of intracellular sulfhydryl groups in general and GSH in particular.

Magnesium, zinc and copper are necessary co-factors in multiple steps of cellular physiological functions and conditions, and are necessary in maintaining among others: eukaryocyte membrane integrity, immune system stability, the synthesis of GSH, the activity of CuZnSOD, the activity of GSHPx, and the modulation of cellular calcium channel gating. All of these activities are impaired in aging and in a variety of the disease states described.

This invention defines and combines physiologically complementary characteristics of GSH precursors and certain metallic salts in: a) clinically effective and balanced formulations; b) appropriate unit dosage forms; c) new therapeutic applications for each.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to a subject suffering from aging or a medical condition. Each unit dosage form typically comprises each of the active ingredients of this invention plus pharmaceutically acceptable excipients. Examples of unit dosage forms are individual tablets, individual capsules, bulk powders, liquid solutions, ointments, creams, eye drops, suppositories, emulsions or suspensions. Clinical alteration of a function or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) physiological functions, conditions or processes in some manner. "Activity" is the ability to perform the function, or to induce or affect the process. Active agents and ingredients are distinguishable from excipients such as carriers, vehicles, diluents, lubricants, binders, buffers and other formulating aids, and encapsulating or otherwise protective components.

"Delivery vehicle" is a composition, which comprises one or more active agents, and is designed to release the active agent in a particular fashion, either by immediately dispersing the agents, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Composition, Formulations and Dosages

Examples of divalent metal forms of thiols that can be used in this invention are magnesium 1-cysteine or magnesium n-acetyl L-cysteine, zinc L-cysteine or zinc n-acetyl L-cysteine and copper L-cysteine or copper n-acetyl L-cysteine. Examples of other dosage forms are n-acetyl L-cysteine ascorbate, magnesium n-acetyl L-cysteine ascorbate, zinc n-acetyl L-cysteine ascorbate, copper n-acetyl L-cysteine ascorbate and the bis forms of L-cysteine, n-acetyl L-cysteine. The invention also contemplates magnesium, zinc and copper formulations that provide metal salt complexes of nac, otc and mpg.

In certain embodiments of the invention, the dosage form is a substantially homogeneous single layer tablet that releases all of its components into the stomach upon ingestion. In certain other embodiments of the invention, the dosage form is a tablet in which the active agents are protected by an acid-resistant coating for release only in the intestine, and optionally in a sustained-release manner over a period of time.

The dosage forms of this invention can be formulated for administration at rates of one or more unit dosage forms per day. Unit dosage forms to be taken three to four times per day for immediate release tablets are preferred. Unit dosage forms to be taken once or twice daily for controlled (sustained) release tablets are preferred.

The polymer matrix of the controlled (sustained) release tablet, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. The rate of diffusion the agent is reasonably constant for the useful life of the matrix (approximately four hours), by which time the incorporated agent is finally depleted and the matrix disintegrates. Such a single layer controlled release tablet, substantially homogenous in composition, is prepared as illustrated in the examples that follow.

The slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of active agents to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the dosage form is a substantially homogeneous single layer tablet that releases all of its components into the stomach upon ingestion.

In certain other embodiments of the invention, the dosage form is a tablet in which the active agents are protected by an acid-resistant coating for release only in the intestine, and optionally in a sustained-release manner over a period of time.

The dosage forms of this invention can be formulated for administration at rates of two or more unit dosage forms per day. Unit dosage forms to be taken three to four times per day for immediate release tablets are preferred. Unit dosage forms to be taken once or twice daily for controlled (sustained) release tablets are preferred.

The amounts of the primary components of the oral dosage form of the pharmaceutical preparation of this invention can vary. Expressed in terms of milligrams per day some examples of components and preferred ranges are illustrated in the following Examples.

However, the following examples are used for illustrative purposes and do not encompass the entirety of the formulations contemplated by the invention, i.e., they are not intended to limit the variety of formulation combinations contemplated by the invention.

EXAMPLE 21

Magensium L-cysteine

IMMEDIATE RELEASE

Magnesium L-Cysteine

| Ranges in milligrams per day | Compound | Magnesium | Cysteine |
|---|---|---|---|
| Preferred | 218 | 11 | 150 |
| to | 3639 | 187 | 2500 |
| Most Preferred | 364 | 19 | 250 |
| to | 1455 | 75 | 1000 |

*SINGLE LAYER UNIT DOSAGE FORM FOR:* Magnesium L-Cysteine

| | tabs / day | | per day | |
|---|---|---|---|---|
| | 3.00 | | mg | mcg |
| TABLET WEIGHT | mg / day | | | |
| 485 | 1455 | Magnesium | 75 | |

FOR SUSTAINED RELEASE

| | | % of formula | milligrams | | | mg | mcg |
|---|---|---|---|---|---|---|---|
| Mg(C5H9NO3S)2 | Magnesium L-Cysteine | 73.83% | 1074.47 | Mag | Cysteine | 1000 | |
| | | | | excipients | | | |
| Mg(C18H35O2)2 | Magnesium Stearate | 0.75% | 10.95 | Mag | Stearate | 10.5 | |
| ... | Starch | 25.42% | 370.00 | | Starch (25%) | 370 | |

AQUEOUS FILM

SUSTAINED RELEASE

Magnesium L-Cysteine

| Ranges in milligrams per day | Compound | Magnesium | Cysteine |
|---|---|---|---|
| Preferred | 205 | 11 | 150 |
| to | 3427 | 187 | 2500 |
| Most Preferred | 343 | 19 | 250 |
| to | 1371 | 75 | 1000 |

*SINGLE LAYER UNIT DOSAGE FORM FOR:* Magnesium L-Cysteine

| | tabs / day | | per day | |
|---|---|---|---|---|
| | 1.00 | | mg | mcg |
| TABLET WEIGHT | mg / day | | | |
| 960 | 960 | Magnesium | 52 | |

FOR SUSTAINED RELEASE

| | | % of formula | milligrams | | | mg | mcg |
|---|---|---|---|---|---|---|---|
| Mg(C5H9NO3S)2 | Magnesium L-Cysteine | 78.40% | 752.56 | Mag | Cysteine | 700 | |
| | | | | excipients | | | |
| Mg(C18H35O2)2 | Magnesium Stearate | 0.76% | 7.30 | Mag | Stearate | 7.0 | |
| ... | Polymer (H2O Sol, Cellulose) | 20.84% | 200.00 | | Polymer (20%) | 200 | |

ACID RESISTANCE FILM

EXAMPLE 22

Zinc L-cysteine

IMMEDIATE RELEASE

Zinc L-Cysteine

| Ranges in milligrams per day | Compound | Zinc | L-Cysteine |
|---|---|---|---|
| Preferred | 12 | 1.5 | 7 |
| to | 1017 | 125 | 623 |
| Most Preferred | 41 | 5 | 25 |
| to | 407 | 50 | 249 |

*SINGLE LAYER UNIT DOSAGE FORM FOR:* Magnesium L-Cysteine

| | tabs / day | per day | |
|---|---|---|---|
| TABLET WEIGHT | 3.00 | mg | mcg |
| | mg / day | | |
| 136 | 407 | Zinc 50 | |

FOR SUSTAINED RELEASE

| | | % of formula | milligrams | | | mg | mcg |
|---|---|---|---|---|---|---|---|
| | | 100% | | | | | |
| $Mg(C_5H_9NO_3S)_2$ | Magnesium L-Cysteine | 73.44% | 298.88 | Zn | L-Cysteine | 249 | |
| | | | | excipients | | | |
| $Mg(C_{18}H_{35}O_2)_2$ | Magnesium Stearate | 0.76% | 3.08 | Mag | Stearate | 3.0 | |
| ... | Starch | 25.80% | 105.00 | | Starch (25%) | 105 | |

*AQUEOUS FILM*

SUSTAINED RELEASE

Zinc L-Cysteine

| Ranges in milligrams per day | Compound | Zinc | L-Cysteine |
|---|---|---|---|
| Preferred | 11 | 1.5 | 8 |
| to | 945 | 125 | 620 |
| Most Preferred | 38 | 5 | 25 |
| to | 381 | 50 | 250 |

*SINGLE LAYER UNIT DOSAGE FORM FOR:* Zinc L-Cysteine

| | tabs / day | per day | |
|---|---|---|---|
| TABLET WEIGHT | 1.00 | mg | mcg |
| | mg / day | | |
| 381 | 381 | Zinc 52 | |

FOR SUSTAINED RELEASE

| | | % of formula | milligrams | | | mg | mcg |
|---|---|---|---|---|---|---|---|
| | | 100% | | | | | |
| $Mg(C_5H_9NO_3S)_2$ | Magnesium L-Cysteine | 78.76% | 300.09 | Mag | Cysteine | 250 | |
| | | | | excipients | | | |
| $Mg(C_{18}H_{35}O_2)_2$ | Magnesium Stearate | 0.77% | 2.92 | Mag | Stearate | 2.8 | |
| ... | Polymer (H₂O Sol, Cellulose) | 20.47% | 78.00 | | Polymer (20%) | 78 | |

*ACID RESISTANCE FILM*

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A process for the synthesis of magnesium bis-N-acetyl-cysteinate salt, said process comprising:

(a) combining approximately 16.3 parts by weight of N-Acetyl-L-cysteine with approximately 5 parts by weight of magnesium carbonate in about 200 ml of water;

(b) stirring the mixture at about 40–50° C. until the evolution of carbon dioxide ceased and then filtered;

(c) washing the collected solids with approximately 200 parts by weight of water; and (d) evaporating water from said solids under reduced pressure to yield dry magnesium-bis-N-acetyl-L-cysteinate salt.

2. A process for the synthesis of zinc bis-N-acetyl-cysteinate salt, said process comprising:

(a) combining approximately 32.6 parts by weight of N-Acetyl-L-cysteine with approximately 13.8 parts by weight of zinc carbonate in about 300 ml of water;

(b) stirring the mixture at about 40–50° C. until the evolution of carbon dioxide ceased and then filtered;

(c) washing the collected solids with approximately 200 parts by weight of water;

(d) evaporating water from said solids under reduced pressure to yield dry zinc-bis-N-acetyl-L-cysteinate salt.

3. A process for the synthesis of copper bis-N-acetyl-cysteinate salt, said process comprising:

(a) combining approximately 32.6 parts by weight of N-Acetyl-L-cysteine with approximately 11.2 parts by weight of potassium hydroxide in about 50 parts by weight of water;
(b) stirring the mixture in an ice bath in a nitrogen atmosphere until a clear solution is obtained;
(c) adding an aqueous solution of approximately 24.2 parts by weight of cupric nitrate trihydrate dissolved in approximately 100 parts by weight of water until precipitation, filtered; and
(d) evaporating water from said precipitate under vacuum to yield dry copper-bis-N-acetyl-L-cysteinate salt.

4. A process for the synthesis of magnesium bis-L-cysteinate salt, said process comprising:
(a) combining approximately 24 parts by weight of L-cysteine with approximately 11.4 parts by weight of magnesium ethoxide in about 100 parts by weight of absolute alcohol;
(b) maintaining the mixture in a nitrogen atmosphere for approximately one hour; and
(c) evaporating solvent from said solids under reduced pressure to yield dry magnesium bis-L-cysteinate salt.

5. A process for the synthesis of zinc bis-L-cysteinate salt, said process comprising:
(a) combining approximately 24.2 parts by weight of L-cysteine dissolved in about 200 parts by weight of stirred water with approximately 13.8 parts by weight of zinc carbonate;
(b) stirring the mixture at approximately 40–50° C. until the evolution of carbon dioxide ceased and filtered;
(c) washing the collected solids with approximately 200 parts by weight of water; and
(d) evaporating water from said solids under reduced pressure to yield dry zinc bis-L-cysteinate salt.

6. A process for the synthesis of copper bis-L-cysteinate salt, said process comprising:
(a) combining in a nitrogen atmosphere a solution of approximately 24.2 parts by weight of L-cysteine dissolved in about 150 parts by weight of stirred water, with approximately 11.2 parts by weight of potassium hydroxide dissolved in approximately 50 ml of water;
(b) adding a solution of approximately 24.2 parts by weight of cupric nitrate trihydrate dissolved in approximately 100 parts by weight of water;
(c) stirring the resulting solution until precipitation is complete, filtered; and
(d) evaporating water from said precipitated solids under vacuum to yield dry copper bis-L-cysteinate salt.

7. A process for the synthesis of magnesium bis-L-2-oxothiazolidine-4-carboxylate salt, said process comprising:
(a) combining a solution of approximately 29.2 parts by weight of L-2-oxothiazolidine-4-carboxylate dissolved in approximately 250 parts by weight of absolute alcohol, with a solution of approximately 11.4 parts by weight of magnesium ethoxide dissolved in about 100 parts by weight of absolute alcohol;
(b) maintaining the mixture in a nitrogen atmosphere for approximately one hour; and
(c) evaporating solvent from said mixture under reduced pressure to yield dry magnesium bis-L-2-oxothiazolidine-4-carboxylate salt.

8. A process for the synthesis of zinc bis-L-2-oxothiazolidine-4-carboxylate salt, said process comprising:
(a) combining a solution of approximately 29.4 parts by weight of L-2-oxothiazolidine-4-carboxylate dissolved in approximately 400 parts by weight of water with approximately 13.8 parts by weight of powdered zinc carbonate;
(b) stirring the mixture at about 40–50° C. until the evolution of carbon dioxide ceased and then filtered;
(c) washing the collected solids with approximately 200 parts by weight of water; and
(d) evaporating water from said solids under reduced pressure to yield dry zinc bis-L-2-oxothiazolidine-4-carboxylate salt.

9. A process for the synthesis of copper bis-L-cysteinate salt, said process comprising:
(a) combining approximately 29.4 parts by weight of L-2-oxothiazolidine-4-carboxylate suspended in about 400 parts by weight of approximately 1:4 ethanol-water, with a solution formed from approximately 11.2 parts by weight of potassium hydroxide dissolved in approximately 50 parts by weight of water;
(b) stirring the mixture until a clear solution resulted;
(c) combining this clear solution with a solution formed by combining 24.2 parts by weight of cupric nitrate trihydrate in approximately 100 parts by weight of water and filtered;
(d) stirring in an ice bath until precipitation is complete and filtered; and
(e) evaporating water from said precipitated solids under vacuum to yield dry copper bis-L-cysteinate salt.

10. A process for the synthesis of magnesium bis-N-(2-mercaptopropionyl)-glycinate salt, said process comprising:
(a) combining a solution of approximately 32.6 parts by weight of magnesium bis-N-(2-mercaptopropionyl)-glycine dissolved in approximately 400 parts by weight of absolute ethanol, with a solution of approximately 11.4 parts by weight of magnesium ethoxide dissolved in about 100 parts by weight of absolute alcohol;
(b) maintaining the mixture in a nitrogen atmosphere for approximately one hour; and
(c) evaporating solvent from said mixture under reduced pressure to yield dry magnesium bis-N-(2-mercaptopropionyl)-glycinate salt.

11. A process for the synthesis of zinc bis-N-(2-mercaptopropionyl)-glycinate salt, said process comprising:
(a) combining in a nitrogen atmosphere, while stirring, approximately 32.4 parts by weight of N-(2-mercaptopropionyl)-glycine suspended in approximately 500 parts by weight of ethanol-water with approximately 13.8 parts by weight of powdered zinc carbonate;
(b) stirring the mixture over night; and
(c) evaporating the alcohol and water from said solids under reduced pressure at approximately 50° C. to yield dry zinc bis-N-(2-mercaptopropionyl)-glycinate salt.

12. A process for the synthesis of copper bis-N-(2-mercaptopropionyl)-glycinate salt, said process comprising:
(a) combining a solution of approximately 1.8 parts by weight of cupric acetate in about 50 parts by weight of ethanol, with a stirred solution of approximately 3.3 parts by weight of N-(2-Mercaptopropionyl)-glycine in approximately 50 parts by weight of water; and
(b) evaporating the solvent and formed acetic acid in a high vacuum of approximately 0.01 mm to yield dry copper bis-N-(2-mercaptopropionyl)-glycinate salt.

13. A process for the synthesis of magnesium N-acetyl-L-cysteinate-L-ascorbate salt, said process comprising:
(a) combining a stirred suspension of approximately 16.3 parts by weight of N-acetyl-L-cysteine and approximately 17.6 parts by weight of L-ascorbic acid in approximately 400 parts by weight of water;

(b) adding approximately 8.4 parts by weight of powdered magnesium carbonate;

(c) stirring the mixture stirred at 40–50° C. until the evolution of carbon dioxide ceased and filtered;

(d) washing the cooled reaction mixture of solids with approximately 200 parts by weight of water; and (e) evaporating water from said solids under reduced pressure to yield dry magnesium N-acetyl-L-cysteinate-L-ascorbate salt.

14. A process for the synthesis of zinc N-acetyl-L-cysteinate ascorbate salt, said process comprising:

(a) combining a stirred suspension of approximately 16.3 parts by weight of N-acetyl-L-cysteine and approximately 12.5 parts by weight of zinc carbonate in approximately 400 parts by weight of water;

(b) adding approximately 6 parts by weight of acetic acid;

(c) stirring the mixture at 40–50° C. until the evolution of carbon dioxide ceased and filtered;

(d) washing the cooled reaction mixture of solids with approximately 200 parts by weight of water; and (e) evaporating water from said solids under reduced pressure to yield dry zinc N-acetyl-L-cysteinate-L-ascorbate salt.

15. A process for the synthesis of magnesium L-cysteinate-L-ascorbate salt, said process comprising:

(a) combining a stirred suspension of approximately 12.1 parts by weight of L-cysteine and approximately 17.6 parts by weight of L-ascorbate in approximately 400 parts by weight of water;

(b) adding approximately 8.4 parts by weight of powdered magnesium carbonate;

(c) stirring the mixture at 40–50° C. until the evolution of carbon dioxide ceased and filtered;

(d) washing the cooled reaction mixture of solids with approximately 200 parts by weight of water; and (e) evaporating water from said solids under reduced pressure to yield dry magnesium L-cysteinate-L-ascorbate salt.

16. A process for the synthesis of copper L-2-oxothiazolidine-4-carboxylate acetate salt, said process comprising:

(a) combining in a nitrogen atmosphere a solution of approximately 14.7 parts by weight of L-oxothiazolidine-4-carboxylate acid and approximately 18.2 parts by weight of cupric acetate in 500 parts by weight of ethanol;

(b) stirring the mixture in a nitrogen atmosphere for approximately one hour;

(c) evaporating solvent from said mixture under reduced pressure; and (d) heating the residue at 40–50° C. in high vacuum (0.01 mm) for several hours to remove the residual acetic acid to yield dry copper L-2-oxothiazolidine-4-carboxylate acetate salt.

17. A process for the synthesis of copper L-2-oxothiazolidine-4-carboxylate chloride salt, said process comprising:

(a) combining in a nitrogen atmosphere a solution of approximately 14.7 parts by weight of L-oxothiazolidine-4-carboxylate acid and approximately 18.2 parts by weight of cupric chloride in 500 parts by weight of ethanol;

(b) stirring the mixture in a nitrogen atmosphere for approximately one hour;

(c) evaporating solvent from said mixture under reduced pressure; and (d) heating the residue at 40–50° C. in high vacuum (0.01 mm) for several hours to remove the residual acetic acid to yield dry copper L-2-oxothiazolidine-4-carboxylate chloride salt.

18. A process for the synthesis of magnesium L-2-oxothiazolidine-4-carboxylate acetate salt, said process comprising:

(a) combining a stirred suspension of approximately 14.7 parts by weight of L-oxothiazolidine-4-carboxylate acid and approximately 8.4 parts by weight of magnesium carbonate in approximately 400 parts by weight of water;

(b) adding approximately 6 parts by volume of acetic acid;

(c) stirring the mixture at 40–50° C. until the evolution of carbon dioxide ceased and filtered;

(d) washing the cooled mixture of solids with approximately 200 parts by weight of water; and (e) evaporating water from said solids under reduced pressure to yield dry magnesium L-2-oxothiazolidine-4-carboxylate acetate salt.

19. A process for the synthesis of zinc N-(2-mercaptopropionyl)-glycine-L-ascorbate salt, said process comprising:

(a) combining a stirred suspension of approximately 15.3 parts by weight of N-(2-mercaptopropionyl)-glycine and approximately 17.6 parts by weight of L-ascorbic acid in approximately 500 parts by weight of ethanol-water (1:1);

(b) adding approximately 12.5 parts by weight of powdered zinc carbonate;

(c) stirring the mixture stirred at 40–50° C. until the evolution of carbon dioxide ceased;

(d) washing the filtered and cooled reaction mixture of solids with approximately 200 parts by weight of water; and (e) evaporating water from said solids under reduced pressure to yield dry zinc N-(2-mercaptopropionyl)-glycine-L-ascorbate salt.

20. A process for the synthesis of magnesium L-2-oxothiazolidine-4-carboxylate hydroxide salt, said process comprising:

(a) combining a solution of approximately 1.5 parts by weight of L-2-oxothiazolidine-4-carboxylic acid dissolved in approximately 25 parts by weight of absolute ethanol, with a solution of approximately 1.2 parts by weight of magnesium ethoxide dissolved in about 10 parts by weight of absolute alcohol;

(b) adding approximately 3 parts by weight of water after approximately 10 minutes;

(c) evaporating solvent from said mixture under reduced pressure; and (d) heating the residue at 40–50° C. in high vacuum (0.01 mm) for several hours remove excess water to yield magnesium L-2-oxothiazolidine-4-carboxylate hydroxide salt.

\* \* \* \* \*